(12) United States Patent
Heckel et al.

(10) Patent No.: US 7,752,913 B2
(45) Date of Patent: Jul. 13, 2010

(54) METHOD AND DEVICE FOR DETECTING DISCONTINUITIES IN A MATERIAL REGION

(75) Inventors: Thomas Heckel, Berlin (DE); Gottfried Schenk, Berlin (DE); Anton Erhard, Berlin (DE); Gerhard Brekow, Berlin (DE)

(73) Assignee: BAM, Berlin (DE)

( * ) Notice: Subject to any disclaimer, the term of this patent is extended or adjusted under 35 U.S.C. 154(b) by 889 days.

(21) Appl. No.: 11/634,778

(22) Filed: Dec. 5, 2006

(65) Prior Publication Data

US 2007/0163348 A1 Jul. 19, 2007

(51) Int. Cl.
*G01N 29/04* (2006.01)

(52) U.S. Cl. .............................. 73/584; 73/602; 73/611; 73/633

(58) Field of Classification Search .................... 73/584, 73/598, 600, 602, 611, 626, 633, 636, 641
See application file for complete search history.

(56) References Cited

U.S. PATENT DOCUMENTS

| | | | | |
|---|---|---|---|---|
| 4,523,468 A | * | 6/1985 | Derkacs et al. | 73/598 |
| 4,611,494 A | * | 9/1986 | Uchiyama | 73/626 |
| 5,119,342 A | * | 6/1992 | Harrison et al. | 367/7 |
| 7,289,938 B2 | * | 10/2007 | Coperet | 702/189 |
| 7,305,885 B2 | * | 12/2007 | Barshinger et al. | 73/602 |
| 7,357,316 B2 | * | 4/2008 | Heckel et al. | 235/383 |
| 7,617,733 B2 | * | 11/2009 | Deemer et al. | 73/660 |

FOREIGN PATENT DOCUMENTS

| | | |
|---|---|---|
| JP | 06 003334 | 11/1994 |
| WO | 2004/074864 | 9/2004 |

OTHER PUBLICATIONS

Erhard et al., "New applications using phased array techniques", Nuclear Engineering and Design vol. 206, 2001, pp. 325-336.
Erhard et al., "Calculation and construction of phased array-UT probes", Nuclear Engineering and Design vol. 94, 1986, pp. 375-385.

* cited by examiner

*Primary Examiner*—J M Saint Surin
(74) *Attorney, Agent, or Firm*—Fay Kaplun & Marcin, LLP

(57) ABSTRACT

A method and a device for detecting discontinuities in a material region having at least one probe which has a plurality of ultrasonic transducer elements and having an evaluation and control device are proposed, in which the transducer elements are disposed diagonally at an angle to the surface of the material region and are actuated via delay elements in such a manner that a defocusing sound field is beamed in. The received signals of the transducer elements are supplied to a plurality of evaluation modules for parallel and simultaneous further processing for different angle values or angle ranges, the number of evaluation modules corresponding to the different angle values or ranges.

17 Claims, 6 Drawing Sheets

METHOD AND DEVICE FOR DETECTING DISCONTINUITIES IN A MATERIAL REGION

FIELD OF INVENTION

The present invention relates to a method and a device for detecting discontinuities in a material region.

BACKGROUND INFORMATION

Ultrasound technique is generally known for the examination of workpieces or material regions. Ultrasound is thereby beamed into the material by means of a probe and the reflection is detected and evaluated. For the examination of rails by ultrasound, a plurality of probes is used which is placed on the stretch of rails, a coupling medium, normally water, being used for coupling the probes to the rail. The probes beam into the rail at respectively different angles and the corresponding reflections are detected and evaluated.

In the case of a rail testing train used at the moment, testing is implemented with the help of respectively 9 probes for 0°, ±20°, ±35° and 2×±70°. However there is a requirement for improvement with respect to extending the probe functions by means of an additional pair of probes of ±55°. Furthermore, the reduction in the use of coupling medium is considered to be necessary, which however counteracts the cited extended use of probes. Also an acceleration in evaluation is regarded as desirable. The technical testing conversion of these development aims is however restricted when using conventional testing technique because the latter is rigid, i.e. it can be adjusted to different track profiles, i.e. rail height, only by means of mechanical retooling, as is the case for the different national rail networks. An increase in the number of probes used in order to obviate this problem is problematic insofar as, as already mentioned, this would result in a greater requirement for coupling medium, which leads above all to supply problems in the case of long travelling distances of the testing train. Also optimal, i.e. flexible adaptation of the acoustic irradiation angles to the testing conditions would be possible only by means of a drastic increase in the probes which are used, which leads to the same problems.

A technically achievable solution would reside in the use of electronically controlled probes, as are used in phased-array technique. It would make respectively only one probe or transducer necessary per rail stretch and travel direction and enable the programme-controlled adjustment of the required angles. Such a technique which has already been used for many years in non-destructive testing with ultrasound and has proved its worth in particular in resolving complex testing tasks, permits optimal adaptation of the sound field parameters, such as acoustic irradiation angle and depth of focus by an electronic route. By reducing the probes to respectively only one phased array probe per rail and direction, furthermore a significant saving in coupling media would be achieved.

From a technical apparatus point of view, the requirement exists hereby however of undertaking the presently required angle adjustments (e.g. 0°, ±35°, ±55°, ±70°) within the travelling speed of the train (maximum 100 km/h) with the required resolution (3 mm). With a time-sequential angle passage as is normal in phased array technique, this is not possible since this would result in a maximum travelling speed of less than 10 km/h. A high travelling speed is however impermissible because of the necessity for adapting to the cycle times of the rail traffic, above all in heavy traffic routes.

SUMMARY OF INVENTION

The present invention relates a method and a device for detecting discontinuities in a material region in which, despite increased relative speed (70 km/h to 100 km/h) between material region and ultrasonic probe or transducer elements, a precise test is possible in a plurality of angle ranges and a rapid corresponding evaluation.

As a result of the fact that the probe has ultrasonic probe or transducer elements which are disposed and actuated in such a manner that a defocusing sound field is beamed into the material, the transmitter elements being disposed diagonally at an angle to the surface of the material and being used to actuate delay elements, and as a result of the fact that the received signals of the elements are supplied in parallel and simultaneously to a plurality of evaluation modules, in which an evaluation of the received signals is undertaken selectively with respect to direction, i.e. respectively for different angle values or angle ranges, the number of evaluation modules corresponding to the different angle values or angle ranges, a testing system is made available which, even at high relative speeds between probe and material region, undertakes testing of the material region in real time.

Hence the requirements of the test practice are taken into account with a significant increase in flexibility with respect to the capacity to adapt to different rail networks. Furthermore, without increasing the number of probes used, an extension of the angle range can be achieved beyond the, at present, normal state if the number of evaluation modules per probe or phased array unit, configured as phased array modules, is extended. This results in an improvement in the test prediction without the disadvantages presented in conventional technique, such as increasing the coupling medium use, and leads to an increase in safety in rail-borne traffic.

BRIEF DESCRIPTION OF DRAWINGS

The invention is represented in the drawing and is explained in more detail in the subsequent description. There are shown.

DETAILED DESCRIPTION

Figure 1:
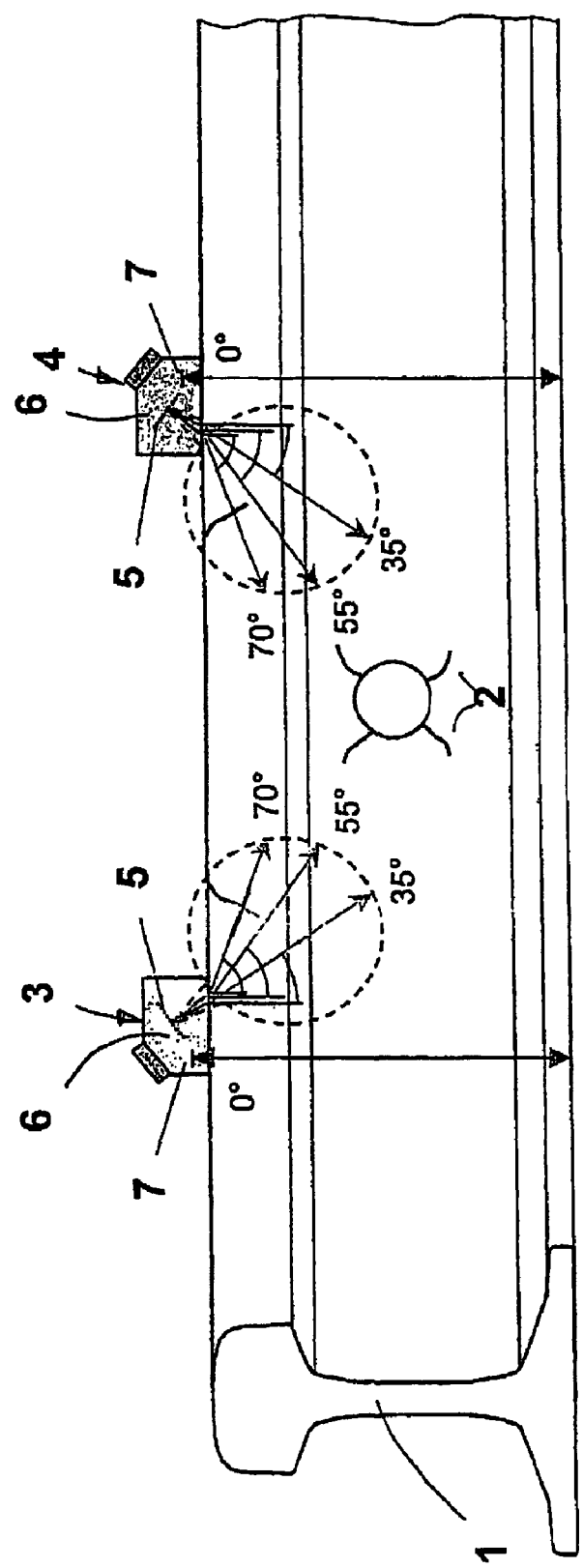
FIG. 1 shows a schematic arrangement of the probes of the device according to an exemplary embodiment of the present invention relative to the rail to be tested.

In the schematic arrangement illustrated in FIG. 1, a rail to be tested is represented with 1, material defects, e.g. cracks, being designated with 2. On the rail 1, probes 3, 4 are disposed, one of which is effective in the travel direction and the other in the counter-travel direction. The probes 3, 4 are configured as ultrasonic phased arrays, the technique of which is based on the physical principle of point source synthesis. The individual elements of a multielement probe are pulsed differently with the help of programmable delay lines so that a sound field formation with variable directivity is generated.

In the illustrated embodiment, the respective probe 3, 4 has a linear arrangement of a fairly large number of ultrasonic array or probe elements 5, e.g. 16 elements. These elements can be configured as piezoelements and they are disposed in a stationary manner on a projecting wedge 6, e.g. made of Plexiglas, in such a manner that a basic acoustic irradiation direction is prescribed, as can be detected in FIG. 1. A suitable electronic control unit, not shown, (as described later) of the individual probe elements enables continuous variation of the acoustic irradiation angle and receiving angle, around the central angle determined by the fixed arrangement, projecting wedge 6, transmitter elements 5, and also the position of the focal point. For example the angles of 35°, 55° and 70° are indicated in the drawing and are prescribed for testing.

The respective probe 3, 4 contains an additional single probe element 7 which is likewise mounted on the projecting wedge 6 and is disposed parallel to the rail and the sound field of which is orientated in the vertical direction. This element 7 serves for coupling control, i.e. to establish whether there is, between probe 3, 4 and rail 1, sufficient coupling of the sound field, normally via a coupling medium such as water. In addition it serves for detection of horizontally orientated defects.

Figure 2:
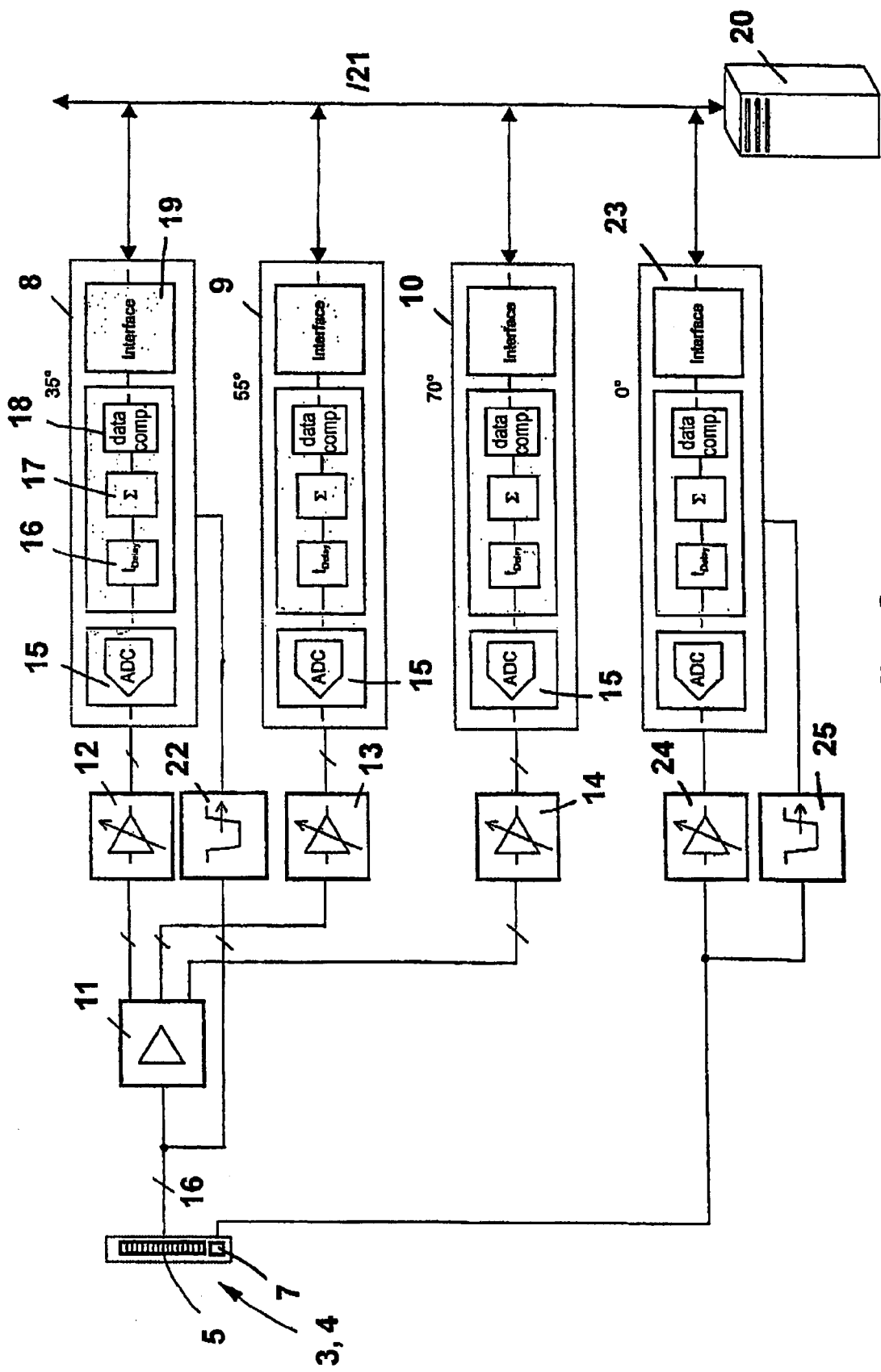
FIG. 2 shows a block diagram of a testing device for one rail and one travel direction.

There is illustrated in FIG. 2 a control and evaluation device for a probe 3, 4, i.e. for a phased shows array with 16 elements 5 and the individual probe element 7 for coupling control. A plurality of phased array modules is assigned to each probe, i.e. to the 16 probe elements 5 and undertakes control and evaluation. The number of phased array modules 8, 9, 10 corresponds to the number of angle values or angle ranges to be evaluated. In the present case, three phased array modules 8, 9, 10 for angle values of 35°, 55° and 70° are assigned to the 16 elements. The 16 elements 5 are connected via 16 lines to a series connection or adapter module 11 which has the function of triplicating respectively received signals present on the 16 lines and supplying them via receiving modules 12, 13, 14 to the respective phased array modules 8, 9, 10. For this purpose, the adapter module 11 has rapid drivers and decoupling elements which distribute the high frequency probe signals respectively to the modules 8 to 10. The receiving modules 12 to 14 which are connected between adapter module 11 and phased array modules 8, 9, 10 have amplifiers with which the echo signals of the transducer elements 5 are adapted to the input dynamics of the AD converters 5 which are indicated further on.

Each phased array module 8, 9, 10 has an AD converter circuit 15 which serves for digitalisation of the analogue echo signals and for metrological processing of the test data. Furthermore, component assemblies are provided for the delay control 16, for the receiving summation 17 and for data compression 18. With the delay control 16, the test signals are "filtered out" in the case of the desired angle ranges or angle values and focusing is undertaken. With the component assembly for data compression 18, compression, rectification or aperture technique can be undertaken. Each module 8, 9, 10 is provided with an interface 19, via which the respective module, as client of a central control and evaluation computer 20, is connected via a rapid bus connection 21 to the latter.

As can be detected from FIG. 2, a transmitting module 22 is connected to the first phased array module 8, on the one hand, and, on the other hand, to the 16 probe elements 5. The transmitting module 22 of the transmitting power stages for excitation of the probe elements 5 contains and delivers the actuation impulses for the phased array with the 16 elements 5 which are configured for example as variable rectangular impulses of high voltage, e.g. 200 V, and which are mutually delayed in such a manner that a defocusing sound field formation is generated which leads to a broad beam directivity. The delay for the respective actuation impulses is delivered from the phased array module 8 and here from the delay component 16 to the emitting module 22.

Finally, another phased array module 23, a receiving module 24 and a transmitting module 25 are provided, which serve for actuation and for signal processing of the individual probe element 7. Basically they have the same construction as the previously described modules, the phased array module 23 being configured for signal processing for an angle value of 0°. It is also connected via the bus system 21 to the control computer 20.

Figure 3:
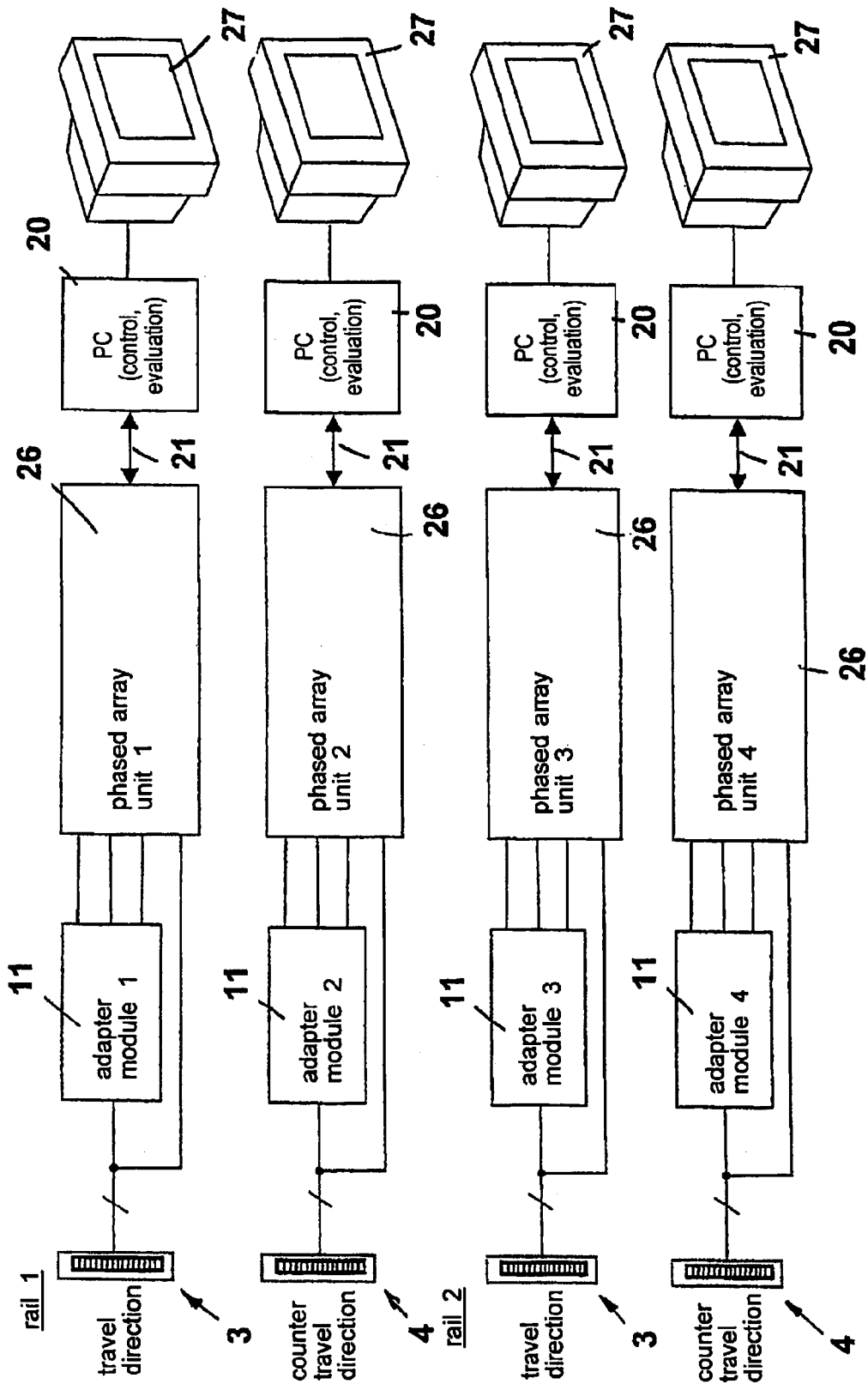
FIG. 3 shows a block diagram of a rail testing system with four probes and corresponding evaluation.

In FIG. 3, a technical apparatus concept for the rail testing is illustrated with four phased array probes, the testing being implemented on both rail elements. In the upper region of the Figure there are illustrated the evaluation elements for the probe 3 which is orientated in the travel direction, and for the probe 4 which is orientated in the counter-travel direction and, in the lower part, the same arrangement for the rail 2. The adapter modules correspond to those according to FIG. 2 and are likewise designated with the reference number 11. A phased array unit 26 is assigned to each probe 3, 4 and is composed of the phased array modules 8, 9, 10, 23 for the different angle values and of the receiving modules 12, 13, 14, 24 and also the emitting modules 22, 25 for the different angle values. The phased array units 26 are connected via the respective bus systems 21 to the respective control and evaluation computer 20, having a corresponding screen 27 for displaying the test results.

Figure 4:
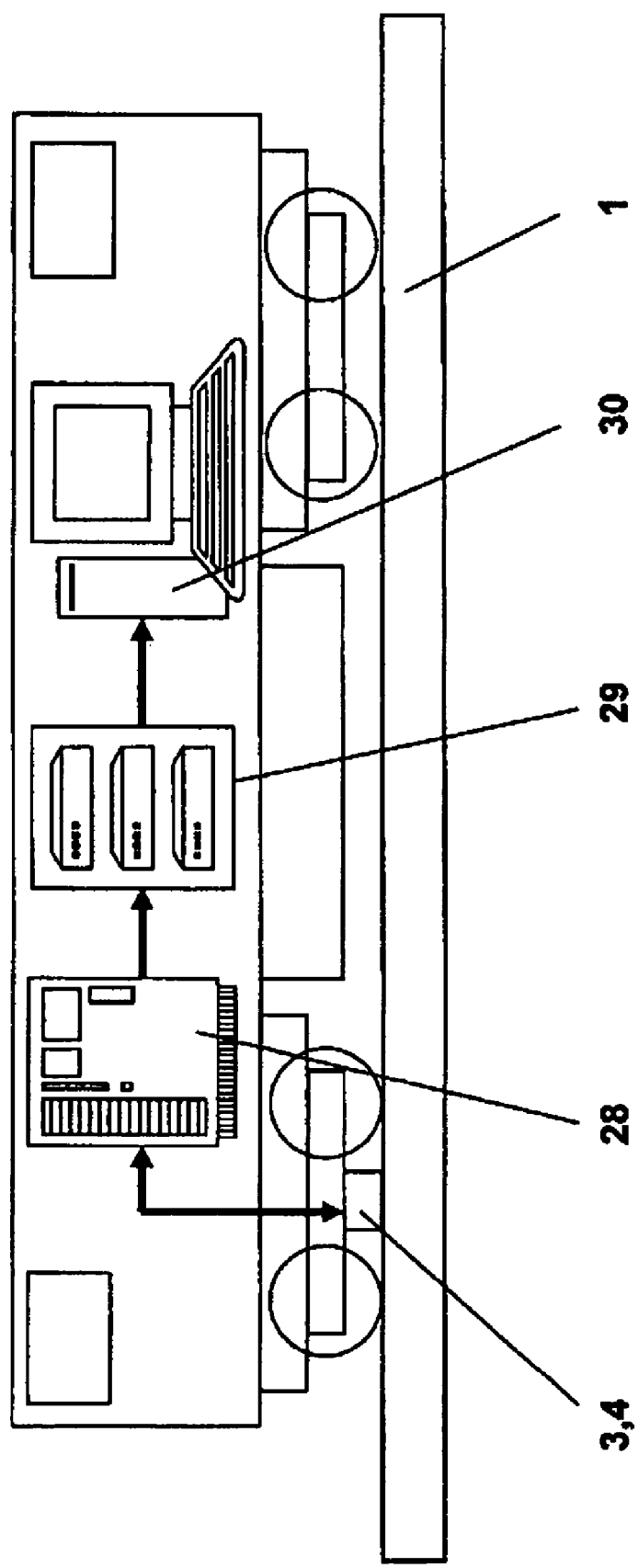
FIG. 4 shows a basic construction of a rail testing train with the test device according to the invention.

FIG. 4 shows a basic construction of a rail testing train with phased array technique, the train including the probe system which comprises the probes 3 and 4 for each rail and also the corresponding supply lines for the coupling medium. The probe system is connected to the phased array apparatus system 28, the measuring data processing unit 29 and the evaluation system 30.

The phased array apparatus system 28 is composed of a number of adapter modules 11 and phased array units 26 which correspond to the number of probes 3, 4 which are used. They are accommodated in a commercially available receiving cabinet which has suitable devices for heat disposal and is connected via the bus system 21 to the measuring data processing unit 29. The measuring data processing unit 29 comprises the already mentioned control and evaluation computers 20 which are fed with the measuring data of the respective phased array units 26. With the help of the control and evaluation computer 20, the received measuring data processed by the phased array units 26 in the already mentioned manner are subjected to a numerical reconstruction which is necessary for the subsequent pictorial display. Furthermore, signal-processing routines, such as noise suppression and digital filtering, can hence be implemented. Following thereon is the evaluation system 30 via which the test findings are evaluated. It comprises a suitable number of monitors 27 on which a number of pictorial online displays of the results are displayed which correspond to the number of probes 3, 4. In addition to manual input aids, such as keyboard, mouse, touch panel, joystick etc. for interactive input of commands and test parameters, it can also contain a monitoring camera for probe control and also an interface to the computer network of the rail operator and a monitor for a possibly present eddy-current testing system. The evaluation system 30 should be disposed in a form which provides an overview for the evaluating tester.

The mode of operation of the previously described system is as follows: as explained, respectively two phased array probes are used per rail and travel direction. With the establishment of an angle value range of e.g. 0°, ±35°, ±55° ±70°, a testing system with in total four phased array units is necessary, which are constructed in turn from four phased array modules. This arrangement is combined in a testing train corresponding to FIG. 4 which travels over the rails. For example a test cycle sequence of 10 KHz is set, as a result of which a travel speed of the rail testing train of approx. 100 km/h with a location resolution of approx. 3 mm is achievable.

Via the respective phased array modules 8 to 10 and the emitting module 22, the respective probe 3, 4 is supplied with actuation signals via 16 channels which generate a frequency of 3 to 5 MHz and, as already described, are mutually delayed or time shifted. As a result, a sound field is beamed into the rail 1 from the respective probe 3, 4 and has a broad beam directivity and for example comprises angle ranges between approx. 30° and 80° in the travel direction and in the countertravel direction. In addition, the individual element 7 is excited via the emitting module 25 with actuation by the phased array module 23, said individual transducer beaming a vertical sound field into the rail, which sound field is reflected at the foot of the rail, this reflection serving to determine the coupling quality.

The sound field reflections are received both by the elements 5 and the element 7 and, in the case of the 16 transducer elements 5, are given to the adapter module 11 via 16 channels. This adapter module decouples the high frequency signals from each other and delivers the received signals to the respective receiving modules 12, 13, 14 via respectively 16 channels which are amplified in the receiving modules 12 to 14 and are subjected to other processing. The thus processed echo signals of the transducer or probe elements are digitalised in the phased array modules 8, 9, 10, as described already, and are processed metrologically into test data, whereupon they are determined via the delay units and summation for the corresponding angle value. Via the interface stages, the data are provided to the evaluation computer 20 for further processing. In this way, the echo signals of a phased array probe can be processed at the same time in the number of phased array modules given by the required angle adjustments.

Figure 6:
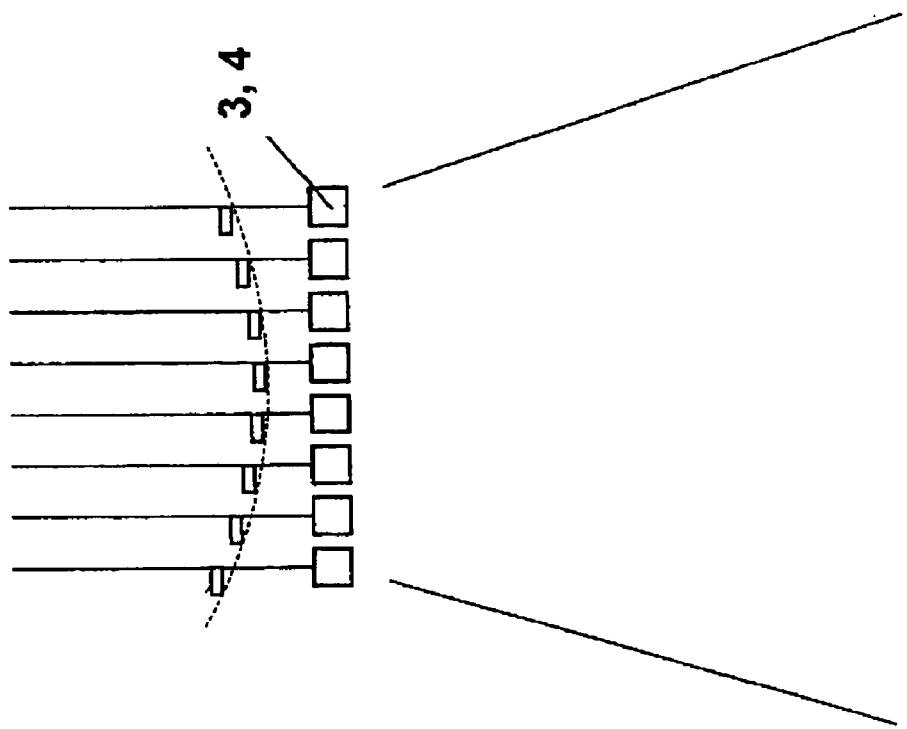
FIG. 6 shows an example of a defocused sound field.
Figure 5:
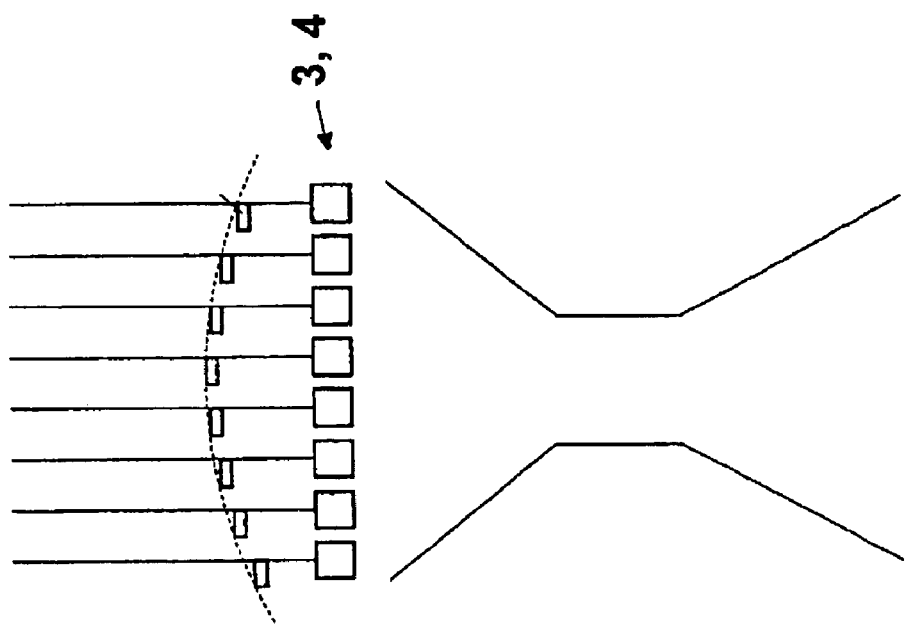
FIG. 5 shows an example of a focused sound field.

FIG. 5 shows an example of a focused sound field, FIG. 6 an example of a defocused sound field.

In order to generate the sound field, the option of running time-controlled phased arrays elements is used, the propagation of the sound bundle being influenced by an electronically controlled running time assignment of the transmitted impulses. Normally this takes place by means of a delay which differs from transducer element to transducer element, said delay being 0 for the outermost elements and the highest value being achieved for the central elements, see FIG. 5. This leads to a constriction of the sound bundle within the near field length of the probe and hence to a variable focus of the sound beam ("focusing").

According to the invention, the opposite effect is used: by an oppositely orientated delay assignment, i.e. with zero delay in the central elements and maximum delay in the edge elements, an artificial sound bundle divergence is produced, see FIG. 6. The delay values for the individual transducer elements are determined numerically for this purpose with the help of special computer program.

The thereby achieved broad beam effect which—as was determined theoretically by means of a probe with 16 elements and verified by metrology—can comprise an angle range of 30° to 80°, is used for the purpose of introducing the sound into the entire volume to be tested with a single transmitting process, i.e. within only one testing cycle. In the case of the conventional—time-sequential—phased array technique, in contrast a sequence of a plurality of transmitting processes and hence a plurality of test cycles are required for this purpose. The method according to the invention, in particular implemented with the device according to the invention, ensures testing of objects which are moving at a relatively high speed, such as rods, pipes or railway rails, in the represented manner.

In particular, in this embodiment, as shown in FIG. 6, the transducer elements of the probes 3, 4 are pulsed with delay in such a manner that a virtual point source transmitter which is common to all transducer elements is produced. The location of the point source transmitter is given here by the intersection lines of the two edges of the sound field.

Figure 7:
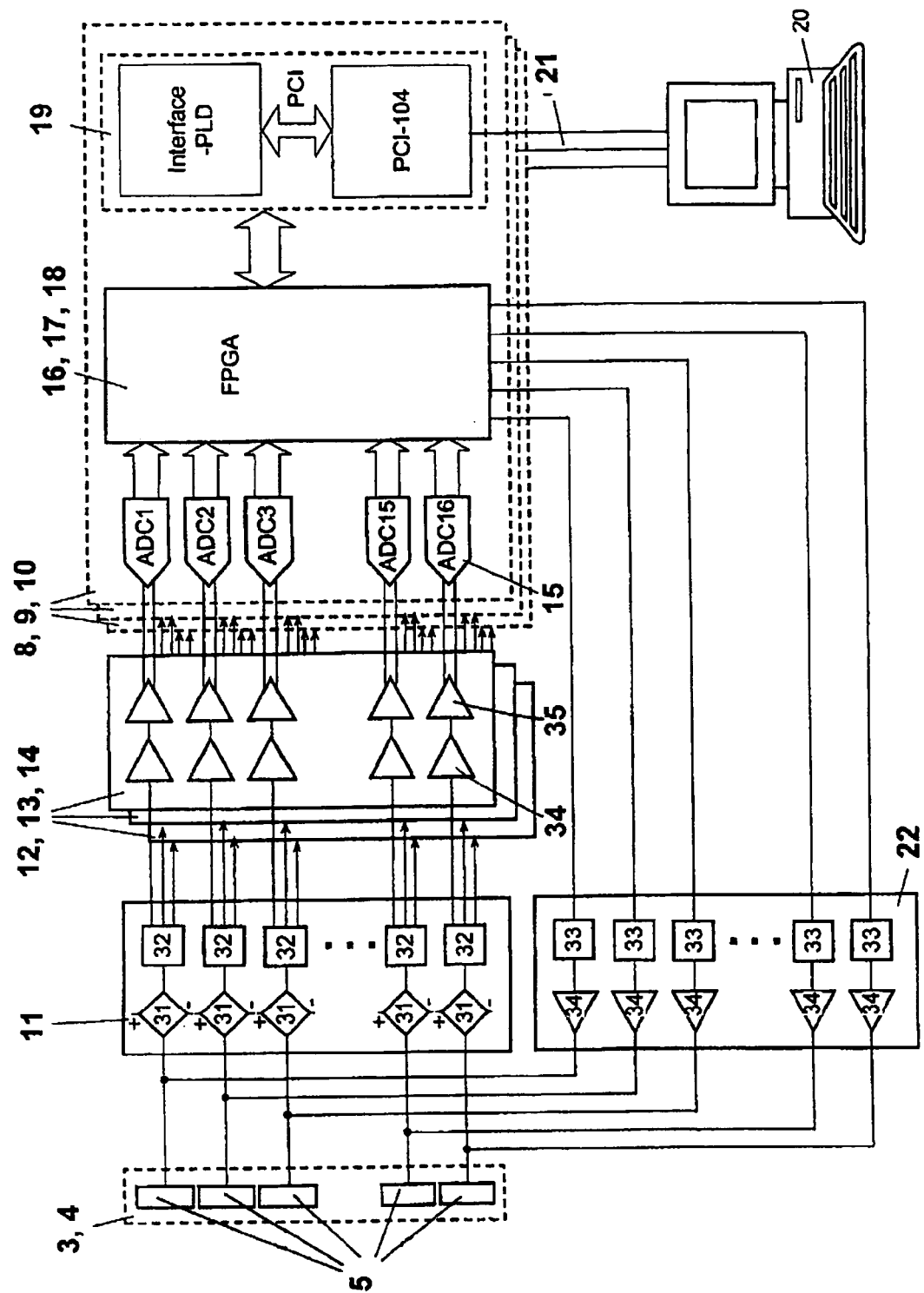
FIG. 7 shows a further block diagram of the test device described in this exemplary embodiment.

FIG. 7 shows in addition to FIG. 2 a further block diagram of the testing device described in this embodiment. The individual transducer elements 7 and the associated electronic control unit 23, 24, 25 are in fact no longer taken into account here.

The received signals of the multielement probes 3, 4 are directed according to the invention via adapter modules 11 to the receiving modules 12, 13, 14 of the respective phased array modules 8, 9, 10 with which the desired angle values for the receiving case are adjusted. The adapter modules 11 have the task of dividing splitting the received signals of a phased array probe 3, 4 and conducting them further to the phased array modules 8, 9, 10 associated therewith. The inputs of the individual receiving modules 12, 13, 14 should thereby preferably be electrically decoupled from each other. Furthermore, the stages should preferably be adapted in their impedance and be low noise. For this reason, no active components are used in this embodiment, which would also be possible in principle, but instead passive power splitters 32 with a corresponding number of outputs and a suitable impedance. A decoupling step 31 precedes each of these components 32 in order to protect the subsequent components from the high transmitting voltage.

The phased array modules 8, 9, 10 correspond in construction and mode of operation to conventional phased array control devices which, in conjunction with the adapter modules 11, enable signal processing in real time within the scope of the method according to the invention.

The phased array modules 8, 9, 10 of the testing device according to the invention comprise, in this embodiment, analogue-digital converters 15, stages for running time delay 16, for summation 17 and for data compression 18, and also filter and interface stages 19. The excitation of the transducer elements can be effected by the transmitting module 22 by means of rectangular pulses with amplitudes of up 250 V and pulse widths of 20 ns up to 2500 ns. A transmitting module 22, in this embodiment, comprises a multiplicity of driver stages 33 and high voltage power amplifiers 34 for this purpose. Hence the transmitting impulse can be adapted optimally to the conditions of the transducer element (frequency, voltage strength, size), which leads to increased sensitivity and hence to an improved signal-to-noise ratio.

In the receiving module 12, 13, 14, adjustable, linear and very low-noise broad band amplifiers 34, 35 ensure exact adaptation of the echo levels to the dynamics of the analogue-digital converters 15. The controlled input dynamics permit an over-all-amplitude range of 50 $\mu V_{ss}$ to 1.5 $V_{ss}$. The bandwidth runs on frequencies of 0.1 MHz to 20 MHz, which covers the spectrum of probe frequencies which are common in practice. For applications in which a path-dependent amplification compensation is required, the amplification can be tracked with a gradient of 40 dB/Ps.

Each receiving channel is equipped with respectively one analogue-digital converter 15. The quantisation depth is 12 bit with a sampling rate of 100 MSPS and analogue input levels of up to 2 $V_{ss}$. Hence the sampling rate, even at a transducer frequency of 20 MHz, is still above the signal frequency by a factor of five, which leads to a high temporal resolution and amplitude stability and requires in particular no subsequent interpolation technique. This reduces the complexity with a simultaneous gain in real time capacity.

The subordinate digital signal processing and control stages are accommodated in a highly integrated programmable component, here an FPGA. As result of the in-circuit programmability, it is possible to adapt the apparatus hardware immediately to changed specifications or test requirements by changing the source codes. The stages 16 contained therein for the running time control of the transducer elements permit a maximum delay value for both the transmitting and receiving case of 20 µs and are adjustable in increments of 1 ns. This meets the prerequisites for controllability of probes with frequencies of 0.5 MHz up to 20 MHz.

The digital summation stages 17 subsequent to the delay stages combine the signals of the individual receiving channels into one summation word. This runs here on 18 bit, an overcontrol bit being contained therein which detects when the maximum or minimum input level of one of the analogue-digital converters 15 is exceeded. It is hence ensured that overcontrols both of the positive and of the negative half-wave in one of the receiving channels are detected and displayed, even if the summation signal has no distortions and is located within the permitted control range. The extremely high dynamics of 17 bit permit subsequent analysis of signals even if these were not picked up with an evaluating amplification and apparently "disappear" in the noise.

The subsequent steps for data compression 18 fulfil the following tasks: the summation signal in original data format, i.e. as a non-compressed HF signal, is intended to be present with support points of 10 ns. This is required for applications such as SAFT (Synthetic Aperture Focusing Technique) or TOFD (Time of Flight Defraction Technique). The HF image is produced in a time window of up to 1.31 ms which can be chosen freely within the test cycle period. This corresponds to a range of 0.03 mm to 3.87 m with longitudinal waves. Then both a two-way rectification and pixelation can be implemented to produce an A-image. The latter can comprise up to 65536 pixels, within a time range of 10 ns to 1.31 ms or 0.03 mm to 3.87 m path for longitudinal wave per pixel, each individual pixel containing the maximum value of the signal range detected by it. Furthermore, for a rapid evaluation of testing regions, even up to 4 apertures can be placed optionally within the evaluation region. These make it possible to detect when a variable adjustable threshold is exceeded, to determine the thereby resulting maximum value and to display the aperture excess as an acoustic or optical signal.

The FPGA contains, in this embodiment, also a digital filter stage for optimising the signal integrity. It concerns filter stages of the Infinite Impulse Response (IIR) type, with which the band width can be restricted with steep edges to the desired frequency range. High-, low- and band-pass configurations of the $4^{th}$ order can be achieved in this way.

A programmable component (PLD) functions together with a single-board PCI-104 computer as interface between the phased array modules 8, 9, 10 and the control and evaluation computer 20.

Connection to the control and evaluation computer is effected here via a gigabit-Ethernet connection 21 using the TCP/IP protocol. This serial bus system is connected on the apparatus side via a corresponding interface of the PC-104 processor board which is present in each of the phased array modules and takes over the interface functions for transmission of the parameter and measuring data.

The invention claimed is:

1. A method for detecting discontinuities in a material region, comprising:
    deploying a probe in a desired configuration relative to the material region;
    activating a plurality of ultrasonic transducer elements of the probe to beam a defocused sound field into the material region, each ultrasonic transducer element being electronically controlled to achieve one of a desired angle and a desired range of angles of irradiation of the material region;
    conducting in parallel a plurality of received signals reflected from the material region to a corresponding plurality of evaluation modules, each evaluation module evaluating a portion of the received signals corresponding to the one of a desired angle and a desired range of angles of irradiation of a corresponding one of the ultrasonic transducer elements; and
    analyzing data assembled by the plurality of evaluation modules to detect discontinuities in the material region.

2. The method according to claim 1, wherein the received signals of the transducer elements are split, wherein after splitting, the received signal are further conducted in parallel to the evaluation modules and then are evaluated in parallel in the evaluation modules for one of an angle value and an angle range which is established respectively there.

3. The method according to claim 1, wherein the transducer elements are disposed so that a fixed acoustic irradiation direction is prescribed, and wherein the individual transducer elements are actuated mutually delayed in order to generate a broad beam directivity.

4. The method according to claim 1, wherein the transducer elements are actuated with delay in order to produce the defocusing sound field in such a manner that a virtual point source transmitter which is common to all the transducer elements is produced.

5. The method according to claim 1, wherein during the parallel, simultaneous further processing, the received signals are respectively digitalized, delayed and summated, one of a desired angle value and a desired angle range being prescribed via the corresponding delay adjustment and being conducted via a bus system to a central computer.

6. The method according to claim 1, wherein a sound field is beamed vertically into the material for coupling control.

7. A device for detecting discontinuities in a material region, comprising:
    at least one probe including a plurality of ultrasonic transducer elements;
    a control device including a plurality of delay elements delaying actuation signals for actuating the transducer elements to generate a defocused sound field; and
    an evaluation device including a plurality of evaluation modules, each of the evaluation modules receiving and processing in parallel a portion of signals reflected from the material region corresponding to one of an angle value and an angle range associated with a respective one of the transducer elements, the evaluation device detecting discontinuities based on data compiled by the plurality of evaluation modules.

8. The device according to claim 7, wherein the transducer elements are connected to an adapter module in order to distribute the received signals, the adapter module being connected to the plurality of evaluation modules in order to conduct the received signals respectively further.

9. The device according to claim 8, wherein the adapter module is configured to split the received signals and conduct them further in parallel to the evaluation modules.

10. The device according to claim 8, wherein the adapter module has at least one passive power splitter to split the received signals.

11. The device according to claim 7, wherein each of the evaluation modules includes a corresponding component assembly for at least one of (i) the digitalization of the analogue received signals delivered from the adapter module, (ii) the delay and angle determination and (iii) the received summation.

12. The device according to claim 7, further comprising:
 a transmitting module actuating the transducer elements with impulses which are mutually delayed respectively.

13. The device according to claim 12, wherein the actuation is undertaken so that a broad beam sound field is produced having an angle range approximately between 30° and 80°.

14. The device according to claim 12, wherein the control device is configured so that a virtual point source transmitter is generated using the delay elements, the virtual point source transmitter being common to all of the transducer elements.

15. The device according to claim 7, wherein the probe includes a single transducer element which is orientated parallel to the surface of the material region, the probe being connected to an assigned evaluation module for coupling control and detection of horizontally disposed discontinuities.

16. The device according to claim 7, wherein the transducer elements are disposed diagonally at an angle to the surface of the material region.

17. The device according to claim 7, wherein for the detection of defects in rails, a first probe is provided for each rail in a travel direction and a second probe is provided for each rail in a counter-travel direction with the corresponding transmitting, adapter and evaluation modules.

* * * * *